United States Patent
Kimmig et al.

(10) Patent No.: US 10,693,257 B2
(45) Date of Patent: Jun. 23, 2020

(54) IMPLANTABLE ELECTROMECHANICAL PLUG CONNECTOR

(71) Applicant: Neuroloop GmbH, Freiburg (DE)

(72) Inventors: Fabian Kimmig, Freiburg (DE); Tim Boretius, Freiburg (DE)

(73) Assignee: Neuroloop GmbH, Freiburg (DE)

( * ) Notice: Subject to any disclaimer, the term of this patent is extended or adjusted under 35 U.S.C. 154(b) by 0 days.

(21) Appl. No.: 16/315,943

(22) PCT Filed: Jul. 6, 2017

(86) PCT No.: PCT/EP2017/066925
§ 371 (c)(1),
(2) Date: Jan. 7, 2019

(87) PCT Pub. No.: WO2018/007517
PCT Pub. Date: Jan. 11, 2018

(65) Prior Publication Data
US 2019/0267755 A1    Aug. 29, 2019

(30) Foreign Application Priority Data
Jul. 6, 2016   (DE) .................. 10 2016 212 332

(51) Int. Cl.
*H01R 13/52* (2006.01)
*A61N 1/375* (2006.01)

(52) U.S. Cl.
CPC ....... *H01R 13/5224* (2013.01); *A61N 1/3752* (2013.01); *H01R 13/5219* (2013.01); *A61N 1/3754* (2013.01); *H01R 2201/12* (2013.01)

(58) Field of Classification Search
CPC ............................ H01R 24/58; H01R 2103/00
(Continued)

(56) References Cited

U.S. PATENT DOCUMENTS 3,988,053 A * 10/1976 Dodenhoff .......... H01R 13/521
                                                         439/887
4,236,525 A * 12/1980 Sluetz ................. A61N 1/3752
                                                         607/38
(Continued)

FOREIGN PATENT DOCUMENTS

DE   10 2011 009 857 B4   9/2012
DE   20 2007 019 606 U1   4/2014
(Continued)

OTHER PUBLICATIONS

International Search Report for PCT/EP2017/066925, dated Oct. 6, 2017; English translation submitted herewith (7 pgs.).

*Primary Examiner* — Gary F Paumen
(74) *Attorney, Agent, or Firm* — Fitch, Even, Tabin & Flannery LLP

(57) ABSTRACT

An implantable electromechanical plug connector is described with a plug part and a socket part, of which the plug part has at least one joining portion which can be inserted completely into a unilaterally open insertion opening within the socket part and has at least one electrically insulating surface having at least one electrode body (6) with a freely accessible electrode surface, and of which the socket part has, inside the unilaterally open insertion opening, an electrically insulating wall portion which laterally delimits the insertion opening at least in part and whose surface makes available at least one counterelectrode body with a freely accessible counterelectrode surface, wherein the electrically insulating wall portion of the electrically insulating surface of the joining portion of the plug part, in the state of complete insertion of the plug part's joining portion in the insertion opening, is oriented in such a way that the counterelectrode surface touches the electrode surface, wherein the at least one electrode body (6) is raised in relation to the electrically insulating surface of the joining portion and/or (Continued)

the at least one counterelectrode body is raised in relation to the surface of the electrically insulating wall portion, and wherein at least one electrically insulating polymer layer is arranged at least in part between the electrically insulating surface of the joining portion and the surface of the electrically insulating wall portion, which polymer layer completely surrounds the mutually touching counterelectrode surface and electrode surface.

54 Claims, 5 Drawing Sheets

(58) Field of Classification Search
USPC .................................................. 439/668, 669
See application file for complete search history.

(56) References Cited

U.S. PATENT DOCUMENTS

| | | | | |
|---|---|---|---|---|
| 4,971,057 | A | * | 11/1990 | Theres ................. A61N 1/3752 607/37 |
| 5,755,743 | A | | 5/1998 | Volz et al. |
| 2003/0163171 | A1 | * | 8/2003 | Kast ..................... A61N 1/3752 607/36 |
| 2005/0118887 | A1 | | 6/2005 | Hoffer et al. |
| 2008/0246231 | A1 | | 10/2008 | Sjostedt et al. |
| 2012/0193119 | A1 | | 8/2012 | Kempf et al. |
| 2012/0315798 | A1 | * | 12/2012 | Poon .................... H01R 13/187 439/668 |
| 2013/0096602 | A1 | | 4/2013 | Kumar |
| 2014/0094048 | A1 | * | 4/2014 | Dilmaghanian ..... H01R 13/187 439/271 |
| 2015/0157853 | A1 | * | 6/2015 | Verzal .................. A61N 1/0551 600/25 |
| 2016/0367819 | A1 | * | 12/2016 | Eldridge .............. A61N 1/3752 |

FOREIGN PATENT DOCUMENTS

| | | |
|---|---|---|
| DE | 10 2012 020 260 B4 | 10/2015 |
| EP | 0 910 435 B1 | 1/2003 |
| EP | 0 811 397 B1 | 3/2005 |
| JP | 2013-094456 A | 5/2013 |
| WO | 2008/025159 A1 | 3/2008 |
| WO | 2009/045772 A1 | 4/2009 |
| WO | 2009/126872 A2 | 10/2009 |

* cited by examiner

IMPLANTABLE ELECTROMECHANICAL PLUG CONNECTOR

CROSS REFERENCE TO RELATED APPLICATIONS

Reference is made to PCT/EP2017/066925 filed Jul. 6, 2017, and German Application No. 10 2016 212 332.7 filed Jul. 6, 2016, which are incorporated herein by reference in their entirety.

BACKGROUND OF THE INVENTION

Field of the Invention

The invention relates to an implantable electromechanical plug connector with a plug part and a socket part.

Description of the Prior Art

In general, electromechanical plug connectors involve two components that can be inserted into each other in a mechanically detachment-resistant manner for the purpose of electrical energy and/or signal transmission and, depending on their design and use, are subject to specific operational safety-relevant requirements. In the case of implantable plug connectors, these must meet the requirements relating to active, implantable medical devices that are exposed to a continually moist environment which they should withstand undamaged in terms of moisture or water penetration into the interior of the implant in question for as long as possible.

Particularly critical in known implantable plug connectors are the joining portions along which the components of the plug connector join to or into each other, usually in a positive or non-positive manner. The particular challenge in designing such plug connectors is preventing the penetration of water or moisture between the plug part and socket part of a plug connector for as long as possible to avoid water or moisture coming into contact with the electrical structures within a plug connector. Water contact on electrically conducting lead and electrode structures, which are mostly metallic, leads to irreversible degradation and an associated impairment of the electrical and signal transmission properties of the plug connector. In addition, the presence of water or moisture can cause detachment of the metallic structures within the plug connector from the surfaces of the components immediately surrounding them, which are usually polymer material, thereby reducing the lifespan of such plug connectors.

A known electrical bushing for use in a housing of an active implantable medical device is described in document DE 10 2011 009 857 B4, the electrical connection structure of which passing through the housing wall is hermetically surrounded by a base body which clings to the housing wall in a fluid-tight manner. The electrical connection structure also opens onto an electrical connection contact within a head part designed as a socket and attached to the housing wall in a fluid-tight manner. The socket comprising at least one electrical connection structure is designed as part of a known standard plug connection.

Document EP 0 910 435 B1 sets out an electrical connection socket for an implantable cardiac pacemaker which comprises an elastically deformable insertion sleeve which in the relaxed state has a curved shape. After insertion of a straight cylindrical contact pin into the sleeve, the latter is forcibly deformed and comes into contact with the outer sides of the straight contact pin forming a largely fluid-tight connection.

Document DE 10 2012 020 260 B1 describes an implantable sub-cutaneous electrical socket and a related percutaneous plug which comprises at least one electrical connection structure for contacting the corresponding funnel-shaped recesses within the socket. The implantable, subcutaneous electrical socket comprises a socket housing through which electrical supply and outlet leads pass for supplying energy and signals to at least one implanted medical device.

Document DE 20 2007 019 606 U1 describes a contact socket for the connection of an electrode lead to an implanted medical device with a socket housing that comprises a connector holder with an elongated holding space. The connector holder comprises a cast component made of a permanently elastic mass into which contact elements of electrically conductive material are inserted.

Described in document EP 0 811 397 B1 is an implantable unit with at least one contact arrangement for connecting an electrical device accommodated in a housing in a hermetically sealed manner with at least one connection cable emerging from the housing which is surrounded by a moulded body made of a non-elastic material and has a freely accessible electrode surface onto which through a pressing force a counter-contact to a continuing connection cable is brought into contact which is surrounded by an elastic material into which a rib-like elevation of the moulded body peripherally surrounding the contact area penetrates forming a positive connection.

Document JP 2013-094 456 A discloses an implantable plug connector with a plug part and socket part in which the electrical contact pins on the plug part side are applied along a cross-sectional area of the plug unit. Joining the contact pins with the contact sleeves on the socket side occurs through axial fitting into each other. The number of electrical contacts is therefore significantly limited by the diameter of the plug connector.

Document US 2005/0118887 A1 describes an implantable plug connector with a plurality of electrode contacts. On an upper side the drawer-like plug unit are electrode contacts which, in the inserted state within the socket part, are pressed by means of a clamping device acting orthogonally on the upper side against the counterelectrode surfaces on the socket part. In the case of intracorporeal application of the plug connector, this requires additional work and instrument use as well as the access necessary for this and space for operating the clamping device, designed in the form of an Allen screw for example.

SUMMARY OF THE INVENTION

The invention further develops an implantable, electromechanical plug connector with a plug part and a socket part which exhibits a high degree of imperviousness to moisture and which prevents moisture-caused material degradation of the electrically conductive structures within the plug connector. Moreover, intracorporeally the implantable plug connector may be manually closed and/or opened easily and without additional joining components. Furthermore, incorrect operation and operation-related damage to the electrode structures within the plug connector is minimized. Finally, despite the plug connector's compact and small three-dimensional shape, it is possible to contact a plurality of electrical transmission leads with the plug connector.

The basis of the invention is set forth in the independent claims. Advantageous, further features of the invention are described in the detailed description, in particular with reference to the illustrated embodiments.

The implantable electromechanical plug connector according to the invention comprises a plug part and a socket part, of which the plug part comprises at least one joining portion which can be inserted completely into a unilaterally open insertion opening within the socket part and has at least one electrically insulating surface having at least one electrode body with a freely accessible electrode surface. The socket part has, inside the unilaterally open insertion opening, at least one electrically insulating wall portion which laterally delimits the insertion opening at least in parts and whose surface provides at least one counterelectrode body with a freely accessible counterelectrode surface, wherein the plug part's electrically insulating lateral wall portion is oriented towards the socket part's electrically insulating surface in the joined together stage where the counterelectrode surface and electrode surface touch each other forming an electrical surface contact. In addition, the at least one electrode body on the plug part is raised in relation to the electrically isolating surface of the joining portion and/or the at least one counterelectrode body on the plug side is raised in relation to the surface of the electrically isolating wall portion. Further, at least one electrically insulating polymer layer is arranged at least in part between the electrically insulating surface of the joining portion on the plug side and the surface of the electrically insulating wall portion on the socket side and laterally completely surrounds the mutually contacting counterelectrode surface and electrode surface.

The at least one electrically insulating polymer layer is preferably made of an elastic material, for example an electrically insulating elastomer, and is firmly joined either to the electrically insulating wall portion or to the electrically insulating surface of the joining portion.

Preferably the at least one electrically insulating polymer layer has a layer thickness which at least corresponds to an orthogonal elevation of the at least one counterelectrode body in relation to the surface of the electrically insulating wall portion or the at least one electrically insulating surface of the joining portion. In this way it is ensured that in the joined state of the plug connector, the contacting electrode and counterelectrode bodies are each fully surrounded by the polymer layer, and that the polymer layer clings flatly to the surface of the electrically insulating wall portion or to the electrically insulating surface of the joining portion in a fluid-tight manner depending on whether the at least one polymer layer is applied on the plug part or the socket part.

In order to minimize penetration of moisture into the plug connector, the size and shape of the joining portion, the size and shape of the insertion opening of the socket part and the size and shape of the electrically insulating polymer layer are matched to each other in such a way that when the joining portion of the plug part is completely inserted into the insertion opening of the socket part, the at least one electrically insulating polymer layer is subjected to a compression force which acts between the surface of the electrically insulating wall portion and the electrically insulating surface of the joining portion. Through the compression force, the polymer layer is pressed flat with increased force to the respective surface of the wall portion or surface of the joining portion, which creates a fluid-tight positive and non-positive connection between the polymer layer and the respective surface.

A further preferred embodiment of the plug connector comprises matching the size and shape of the joining portion, the insertion opening, the at least one electrically insulating polymer layer and the respective electrode and/or counterelectrode bodies to each other so that the contacting electrode and counterelectrode surfaces are in mutual contact through the effect of pressing force. As the further embodiments show, the pressing force may be predefined through a particular elevation of the at least one electrode body or counterelectrode body in relation to the respective surface.

In a further preferred embodiment, the polymer layer is a hygroscopic material which swells on contact with moisture or water, which increases the compression effect on the polymer layer and also improves the sealing effect.

The at least one polymer layer is preferably polydimethylsiloxane, PDMS for short, or LPC (liquid crystal polymer) or parlylene. Alternative, biocompatible polymer or elastomer materials, such as polyimide, are also suitable. The aforementioned swelling effect can advantageously be brought about through incorporating hygroscopic components or compounds into the polymer layer, e.g. through the interspersion of salt crystals in a PDMS layer or through the provision of crystalloid, hygroscopic intermediate layers in a layered polymer layer composite. Also suitable as hygroscopic components are silica gel, activated clay, chemical water binders, zeolite, cellulose.

All of the components of the plug connector of the present invention are made of biocompatible materials to comply with the medical approval conditions. Particularly suitable materials for producing the at least one electrode body and counterelectrode body are metals, such asgold, platinum or iridium or metal alloys. Instead of metallic electrode materials, it is also possible to use conductive polymer materials, such as PEDOT.

In a further preferred embodiment, the plug part is flat or plate-shaped and has an upper and lower side. The joining portion of the plug part has a longitudinal and transverse direction, wherein the length of the joining portion in its longitudinal direction corresponds with an insertion depth of the insertion opening on the socket part side such that in the joined state the joining portion completely enters the insertion opening. Projecting out of the plug part is a plug portion, adjoining the joining portion in one piece, on which at least one electrical contact is provided, which is electrically connected to the at least one electrode surface provided in a joining portion. The at least one electrical contact acts as an electrical connection electrode to a lead wire, which, for example, is connected to the electrical contact by way of a soldered connection.

Along the inside of the insertion opening on the socket part at least one insertion guide is provided on the wall, along which the joining portion on the socket part slides during insertion. In a preferred embodiment, the insertion guide has a first section, along which the joining portion can only be inserted in its longitudinal direction. Adjoining the first section along the insertion guide is a second, rear section, along which the joining portion can be further inserted in its longitudinal and transverse direction. By way of the second section the socket part is deflected relative to the plug part diagonally to the longitudinal insertion direction and reaches an end position with a lateral offset relative to the initial longitudinal insertion direction.

During insertion of the plug part into the socket part, in which the plug part is forcibly guided along the first section of the insertion guide, the at least one electrode body and counterelectrode body are at a lateral distance relative to each other and do not come into mutual contact. Particularly in the case of multiple electrode bodies on the joining portion and a corresponding number of counterelectrode bodies on at least one surface of the electrically insulating wall portion on the plug part, the electrode surfaces of the electrode bodies on the plug part slide past the counterelectrode surfaces of counterelectrodes on the socket part in a contactless manner. Only through the diagonal or sideways movement that finalizes the procedure of joining the plug part within the insertion opening do the electrode surfaces come into contact with the counterelectrode surfaces assigned to them. In this way unnecessary wear-associated oversliding and grinding between electrode and counterelectrode surfaces during the joining procedure is reduced to a minimum.

In addition although the plug part at least partially comes to rest in the end position in a so-called "undercut area," appropriate designing of the plug part and socket part makes penetration of moisture or water impossible or at least considerably more difficult. In particular, in the end position, areas of the side walls of the plug and socket part are in internal contact through which the entrance opening of the insertion opening is completely closed in a fluid-tight manner between the plug and socket part.

Essentially the socket part forms a type of insertion housing for the plug part. The housing is preferably made of a rigid, dimensionally-stable biocompatible material, preferably titanium or a ceramic. The housing surrounds the unilaterally open insertion opening completely so that all forces acting on the housing are distributed along closed force paths.

Preferably the at least one polymer layer is firmly joined to the electrically insulating wall portion within the insertion opening of the socket part that has a freely accessible counterelectrode surface and the at least one counterelectrode surface has a recess so that it is completely and seamlessly surrounded by the polymer layer.

In contrast, the electrode body on the plug part projects upwards over the electrically insulating surface of the joining portion which, during insertion into the insertion opening of the socket part, locally compresses the elastic polymer layer to fit precisely into the recess in the polymer layer on the counterelectrode surface. In this state the polymer layer clings seamlessly to the outer contour of the electrode body.

Alternative embodiments are conceivable with two electrically insulating wall portions arranged opposite each other in the plug part on each of which a polymer layer is applied. It is also possible to firmly apply a polymer layer to the at least one electrically insulating surface in the joining portion of the plug part.

The plug connector according to the invention is also characterised by a compact and small three-dimensional shape which, depending on the number of electrode and counterelectrode bodies within the plug connector, can have a plug connector length and width of a few mm to a few cm.

Advantageously, at least the plug part can be produced as part of a multilayer process. Depending on the number of electrode bodies in the joining portion of the plug part, electrical connection structures must be formed within the plug part as part of the manufacturing process. The electrical connection structures can be designed as individual electrical layers within a stacked layer composite and/or in the form of strip conductors each applied separately on an intermediate layer surface, for which electrical connections to the electrical contacts and the electrode bodies must be created.

Advantageously, for manufacturing the plug part, multilayer ceramic technology is used, preferably to produce low-temperature co-fired ceramics, LTCC, or high-temperature co-fired multilayer ceramics, HTCC. For producing the at least one electrode body raised above the electrically insulating surface of the joining portion, thick film technology can be used, with which layer depositions with layer thicknesses in the μm-range or above can be produced. Alternatively it is possible to produce the raised electrode body structures by applying a conductive film or paste over the entire area of electrically insulating surface of the joining portion, which is subsequently structured, preferably by laser radiation. Galvanic deposition techniques are also suitable for producing the electrode body structures.

The plug connector according to the invention is particularly suitable for contacting multiple electrode and counterelectrode bodies on the plug part and socket part in order to contact as many electrical transmission channels as possible. The electrode bodies on the plug part are arranged on the at least one electrically insulating surface, which on insertion of the plug part into the socket part is orientated in parallel or essentially in parallel to the insertion direction. In this way, through appropriate selection of the shape and size of this surface, sufficient space can be created for accommodating a large number of electrode bodies, without increasing the diameter of the implantable plug connector, as it must be kept as small as possible. In a similar manner the counterelectrode bodies are applied to the at least one electrically insulating wall portion laterally delimiting the insertion opening.

To further increase the number of electrode and counterelectrode bodies on the plug part and socket part, the plug part preferably has two electrically insulating surfaces which are opposite and orientated away from each other and preferably have multiple electrode bodies each with a freely accessible electrode surface. Equally, within the unilaterally open insertion opening the socket part has two electrically insulating wall portions which are opposite and orientated towards each other, the surfaces of which comprise the same number of counterelectrode bodies each with a freely accessible counterelectrode surface. The electrically insulating wall portions on the socket part are each orientated towards one of the electrically insulating surfaces of the plug part in the joined state so that the counterelectrode surfaces directly and indirectly touch the electrode surfaces. In this way miniaturized plug connectors can be produced which can connect up to 256 separate electrical transmission channels, preferably up to 50 transmission channels, to each other.

It is also conceivable to apply additional electrode bodies on a side wall area which connects the two aforementioned electrically insulating surfaces each orientated away from the other.

Further details concerning the design of the plug connector according to the solution are set out in the further description with reference to the examples of embodiment.

BRIEF DESCRIPTION OF THE DRAWINGS

The invention will be described below without restricting the general inventive concept by way of examples of embodiment with reference to the drawings. Here.

DETAILED DESCRIPTION OF THE INVENTION

Figure 1:
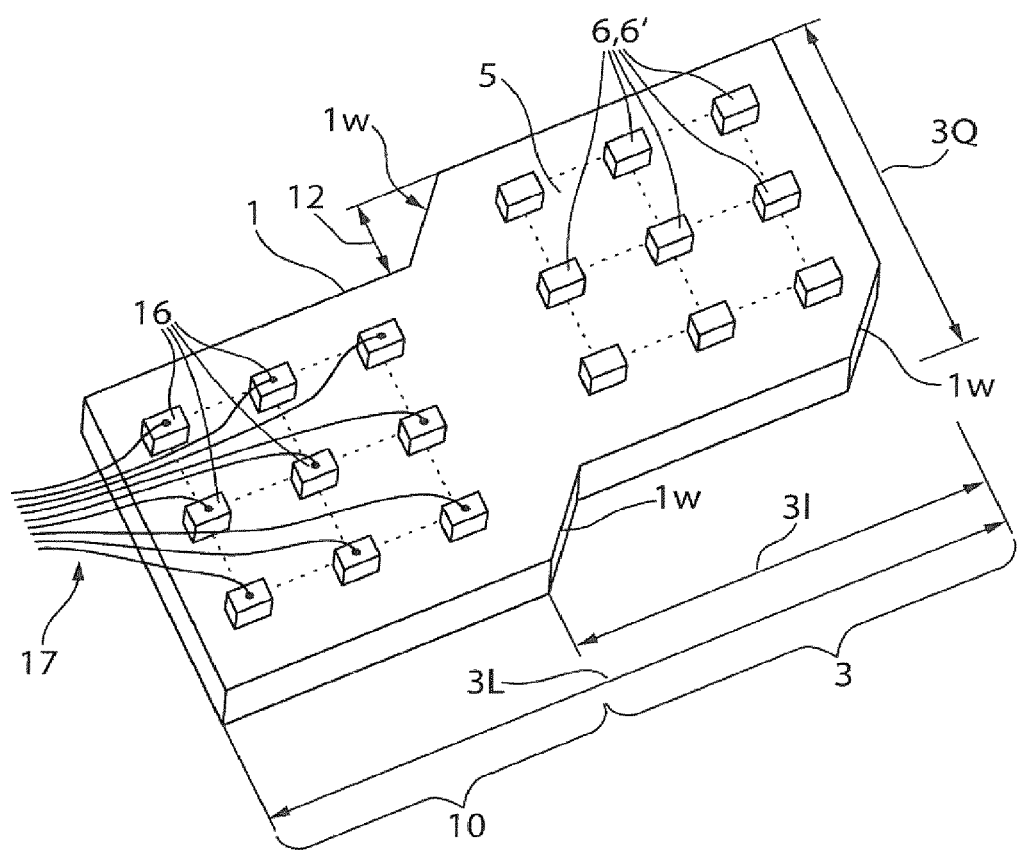
FIG. 1 shows a schematic, perspective view of a plug part.

FIG. 1 shows a perspective, schematic view of a plug part 1 which is essentially plate-shaped and has a longitudinal direction 3L and a transverse direction 3Q. The plug part 1 comprises a joining portion 3 which has a longitudinal direction 3I and is insertable into a socket part illustrated in more detail in FIG. 2. Connected in one piece with the joining portion 3, the plug part 1 comprises a plug portion 10, which in the joined state within the socket part, explained in more detail in FIG. 2, projects out of the socket part 2. Structural modifications are of course conceivable in which the plug part has space over its entire length within the socket part.

The plug part 1 shown in FIG. 1 has an electrically insulating surface 5 which extends uniformly both in the plug portion 10 and the joining portion 3.

In this embodiment, in the joining portion 3 of the plug part 1 nine electrode bodies 6 are arranged, each having an upper electrode surface 6'. Correspondingly, in the plug portion 10 nine electrical contacts 16 are also provided on which, via, for example, soldered connections or similar electrical joining techniques, electrical supply/outlet leads 17 are fastened. The electrical contacts 16 envisaged on the plug part side are electrically connected in a suitable manner within the plug part 1 with electrode bodies 6 arranged in the joining portion 3. Plug connections are conceivable which can provide 40, 50 and more electrode bodies 6 on the surface 5.

The plug part 1 shown in FIG. 1 is also characterized by a side or lateral offset 12 via which the joining portion 3 is arranged laterally of the plug portion 10. For this two plug part side walls 1w extending diagonally to the longitudinal direction 3L are provided between the joining portion 3 and the plug portion 10. The plug part 1 also has a correspondingly dimensioned side wall 1 on the end face of the joining portion 3.

Figure 2A:
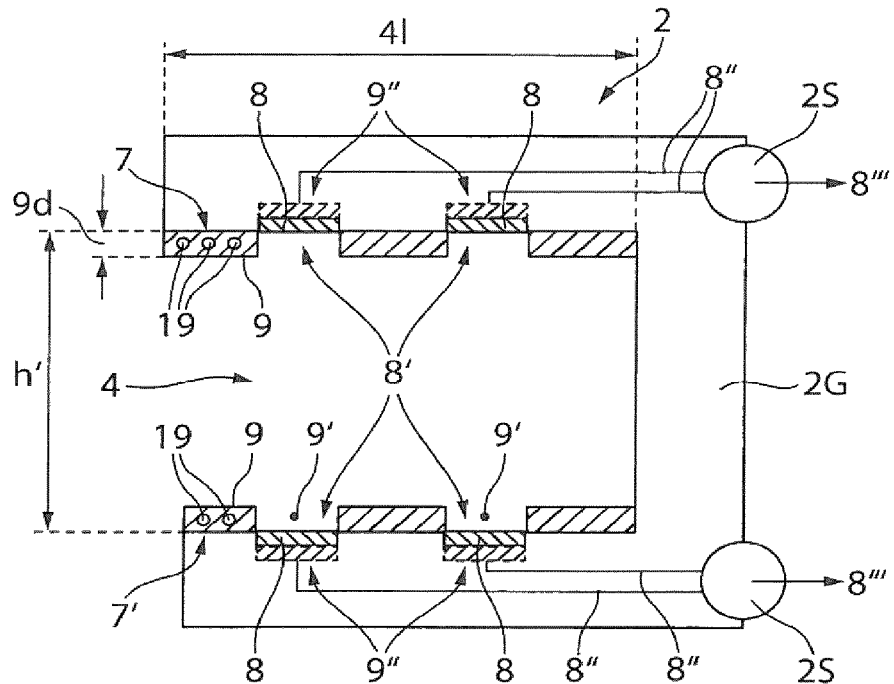
FIGS. 2a, and b show a longitudinal section as well as a perspective view of a socket part.
Figure 2B:
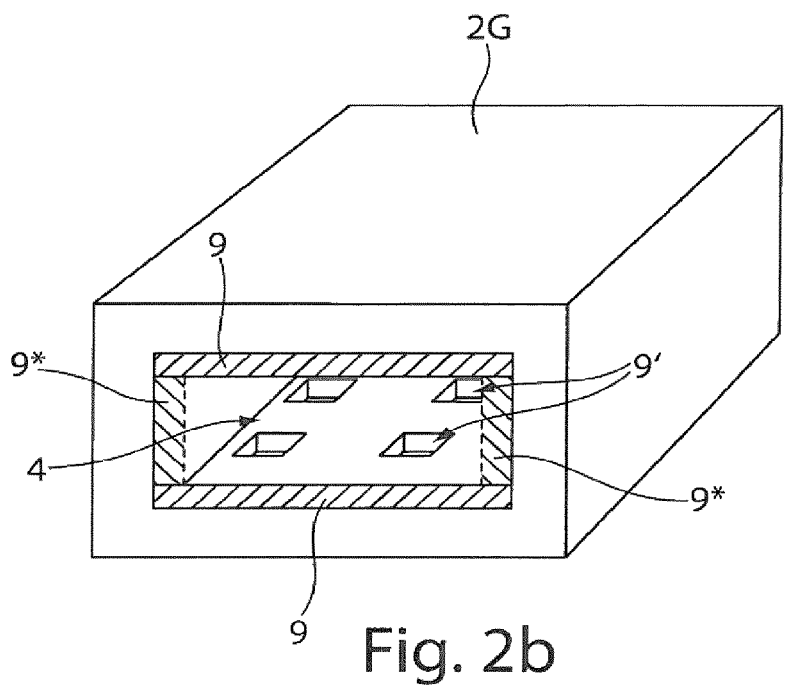

In FIG. 2a a longitudinal section through a socket part 2 is illustrated. FIG. 2b shows a perspective view of the socket part 2 which has an insertion opening 4 into which joining portion 3 of the plug part 1 can be completely inserted on the front side. The socket part 1 comprises a dimensionally stable housing 2G and in the illustrated example of embodiment has two oppositely located electrically insulating wall portions 7, 7' on the surfaces of which counterelectrode bodies 8 each with freely accessible counterelectrode surface 8' are arranged. The counterelectrode bodies 8 are connected by way of electrical connection leads 8''' integrated in the housing 2G and an electrical interface 2S with an electrical lead 8'' or several leads 8'' leading away from the housing 2G.

Firmly connected to the electrically insulating wall ports 7, the socket part 2 comprises an electrically insulating polymer layer 7 which has a polymer layer thickness 9d and comprises recesses 9' which are each matched to the counterelectrode surfaces 8' so that the polymer layers 9 peripherally surround the counterelectrode surfaces 8' preferably in a flush and fluid-tight manner. Optionally, under each counterelectrode body 8, i.e. between the dimensionally stable, rigid housing 2G and each counterelectrode body 8 there is also a polymer layer 9''. In this way the counterelectrode body 8 is borne elastically relative to the housing 2G, which is advantageous in the case of force-effected contacting with a corresponding electrode body 6.

The configurations of the socket part and plug part 2, 1 are matched to each other accordingly, meaning that the number and arrangement of the counterelectrode bodies 8 provided in the socket part 2 correspond to the number and arrangement of the electrode bodies 6 applied in the plug part 1. The shape and dimensions of the insertion opening 4 within the socket part 2 are matched to each other in accordance with the shape and size of the joining portion 3 of the plug part 1. In the case of the socket part 2 illustrated in FIG. 2, a suitably designed plug part 1 would have four electrode bodies on both the upper side and lower side of the joining portion 3.

Figure 3A:
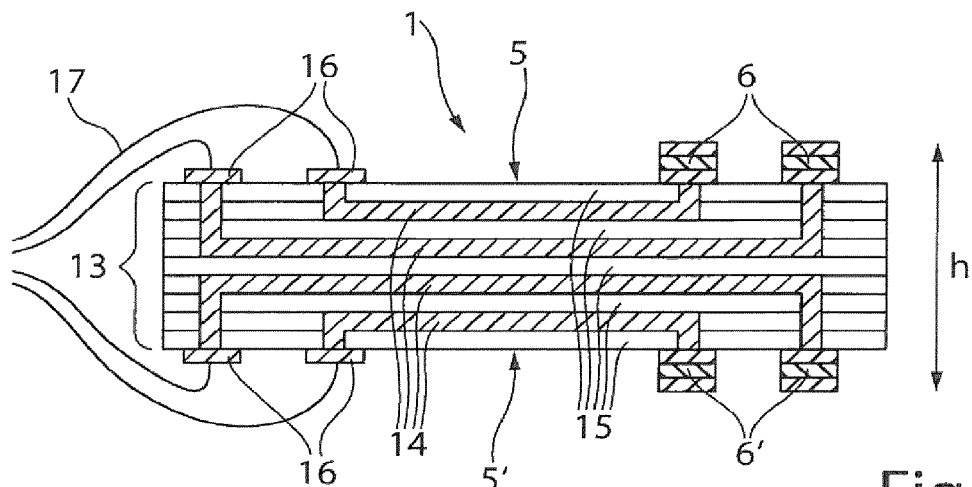
FIGS. 3a, b and c show longitudinal sectional views through alternative plug parts.

A longitudinal section through a plug part 1 with four electrode bodies 6 applied on both the upper and lower side of the joining portion 3 is illustrated in FIG. 3a. The plug part 3 comprises a stack layer composite 13 with a sequence of electrically conducting layer areas 14 and electrically insulating layer areas 15. Suitable for producing the stack layer composite 13 are multilayer processes which allow the manufacturing of so-called low-temperature co-fired ceramics (LTTC) or high-temperature multilayer co-fired ceramics (HTTC). The electrical layer areas 14 are preferably made of gold, platinum or iridium, whereas the electrically insulating layer areas 15 preferably are ceramic materials.

The plug connector 1 illustrated in FIG. 3a envisages electrode bodies 6 as well as electrical contacts 16 on both the upper and lower side. The electrical contacts 16 serve to form soldering points for connecting electrical connection cables 17. Preferably the electrical contacts 16 as well as the electrode bodies 6 are produced by way of thick film technology, for example by way of screen printing. Film or coating layer applications to the surfaces 5, 5' can also be used. The applied coating layer or film is then processed and structured, by means of laser radiation for example.

It is also conceivable to provide the plug connector 1 shown in FIG. 3a with an additional electrode body which is arranged along a side edge of the stack layer composite 13 to further increase the number of electrode bodies.

The plug part 1 is dimensioned according to the dimensioning of the socket part 2. The total thickness h of the plug part 1 in the joining areas 3 including the electrode body 6 raised above the surfaces 5, 5 is slightly smaller than the maximum opening width h' of the insertion opening 4 within the socket part 2. In this way the polymer layers 9 are compressed on insertion of the plug part 1 into the socket part 2 shown in FIG. 2 a, b and on reaching the end position of the plug part 1 within the socket part 2 the electrode bodies 6 enter the recesses 9' of the polymer layer 9, wherein the electrode surfaces 6 as well as counterelectrode surfaces 8' arranged opposite them come into close electrical area contact. In the end position the polymer layers 9 completely surround the electrode bodies 6. In addition, through the effect of compression forces the polymer layers 9 cling to the surfaces 5 within the joining portion 3 of the plug part 1. Penetration of moisture into the area of the electrode bodies 6 is thus minimized along the interface between the upper and lower side of the plug part 1 and the polymer layers 9.

In order to increase the blocking effect against the penetration of water or moisture along the side walls of the plug part and the socket part 2, additional polymer layers 9* can optionally be applied to the side wall areas within the insertion opening 4, preferably on the socket part side, see the polymer layers 9* shown by the dashed line in FIG. 2b.

Furthermore, for further improving the blocking effect the polymer layers 9 of 9* can at least in parts be combined with hygroscopic material components 19 which in the presence of moisture bind water and thereby cause the polymer layer 9, 9* to swell. See FIGS. 2a and b. Through the swelling-induced increase in volume of the polymer layer 9 the compression force acting on the polymer layer 9 directly increases as does the associated blocking effect or sealing function with regard to moisture or water penetration. Preferably the hygroscopic material components 19 are provided in areas of the polymer layer 9, 9* close to the opening area of the insertion opening 4. For the sake of as uniform a blocking effect as possible the entire polymer layer 9 can be mixed or enriched with hygroscopic material components.

Figure 3B:
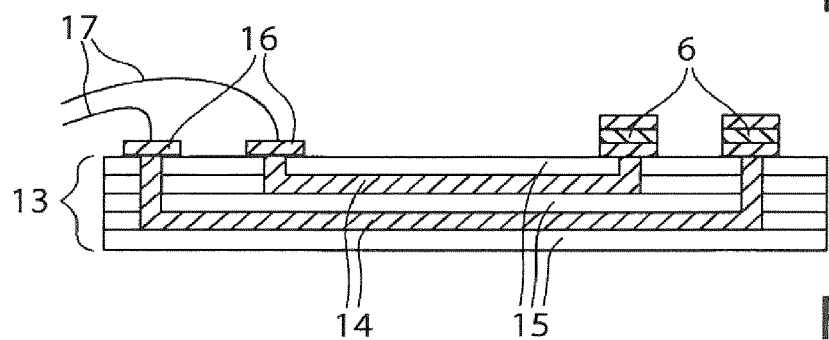
Figure 3C:
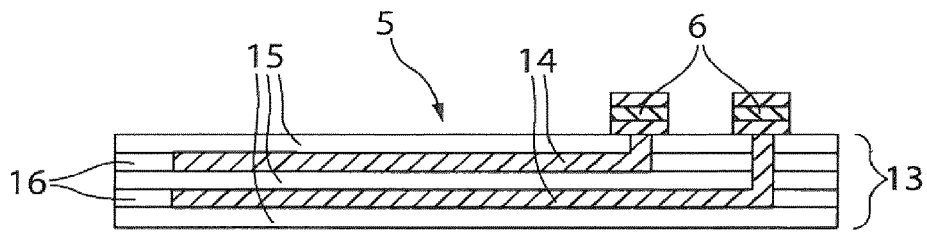

A further alternative embodiment for the plug part 1 is illustrated in FIG. 3b, which in contrast to the plug connector shown in 3a only has electrical contacts 16 and electrode bodies 6 on the upper side of the stack layer composite 13. As an alternative to producing electrical contact points 16 on the surface within the plug portion 10, the electrical contacts 16 in the example shown in FIG. 3c are designed as plug contact sockets in lateral extension to the individual electrical layer areas 14.

Figure 4:
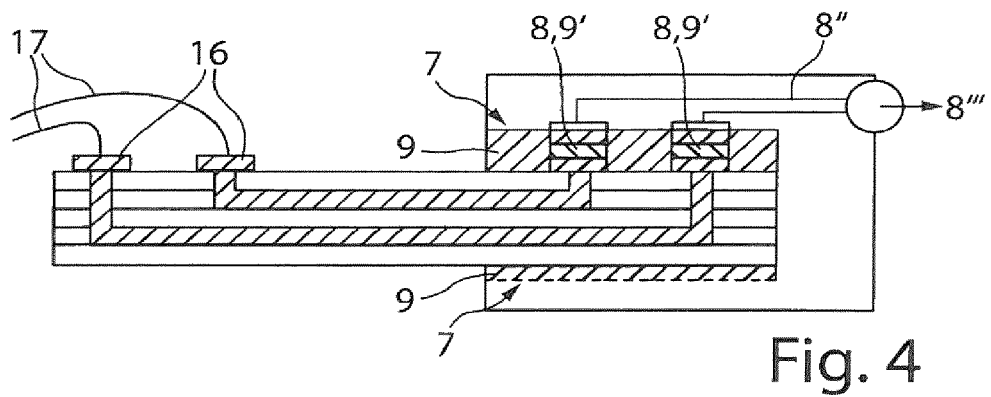
FIG. 4 shows a longitudinal sectional view of a plug part inserted into a socket part.

FIG. 4 shows a longitudinal section of the plug connector 1 illustrated in FIG. 3b with an appropriately prepared socket part 2. The electrode bodies 6 of the plug connector 1 are located within the recesses 9' of the polymer layer 9 which is firmly attached on the upper electrically insulating wall section 7. Optionally a further polymer layer 9 can be applied on the lower electrically insulating wall section 7. Moisture penetration into the intermediate gap between the electrically insulated surface 5 of the plug part 1 and polymer layer 9 is minimized, especially as the polymer layer is pressed onto the surface 5 of the plug part 1 due to appropriate selection of its thickness and is subject to an additional compression force and an associated pressing force increasing the sealing effect. In the illustrated joined state the electrode and counterelectrode surfaces are in close electrical area contact so that the plug connector produces an electrical connection between the cables 17 and 8''''.

All electrode and counterelectrode bodies 6, 8 as well as the electrode and counterelectrode surfaces 6', 8' connected thereto can assume any three-dimensional shapes. Thus, n-angled, oval, round circumferential edges are suitable for configuring the electrode and counterelectrode surfaces 6', 8'.

Preferably the freely accessible electrode surfaces (6') of the electrode bodies (6) are orientated in parallel or obliquely to the at least one electrically insulating surface (5, 5'), just as the freely accessible counterelectrode surfaces (8') of the counterelectrode bodies (8) are orientated in parallel or obliquely to the electrically insulating wall portion (7, 7').

Additionally or alternatively the normal surfaces of the electrically insulating surfaces (5, 5') as well as of the electrically insulating wall portion (7, 7') are each orientated orthogonally or obliquely to the insertion direction along which the joining portion of the plug part can be guided into the insertion opening (4) of the socket part (2).

In a departure from a mathematically strictly defined parallelism or orthogonality, "oblique orientation" in the above sense should be taken to be an angle tolerance α of maximum α=±30°.

The insertion direction is predetermined by the shape and design of the plug part and socket part, and is, as shown in the further statements relating to FIGS. 5a to 5d, initially orientated along a spatial axis. The plug part is also moved longitudinally and transversely in relation to the first direction in space.

Figure 5A:
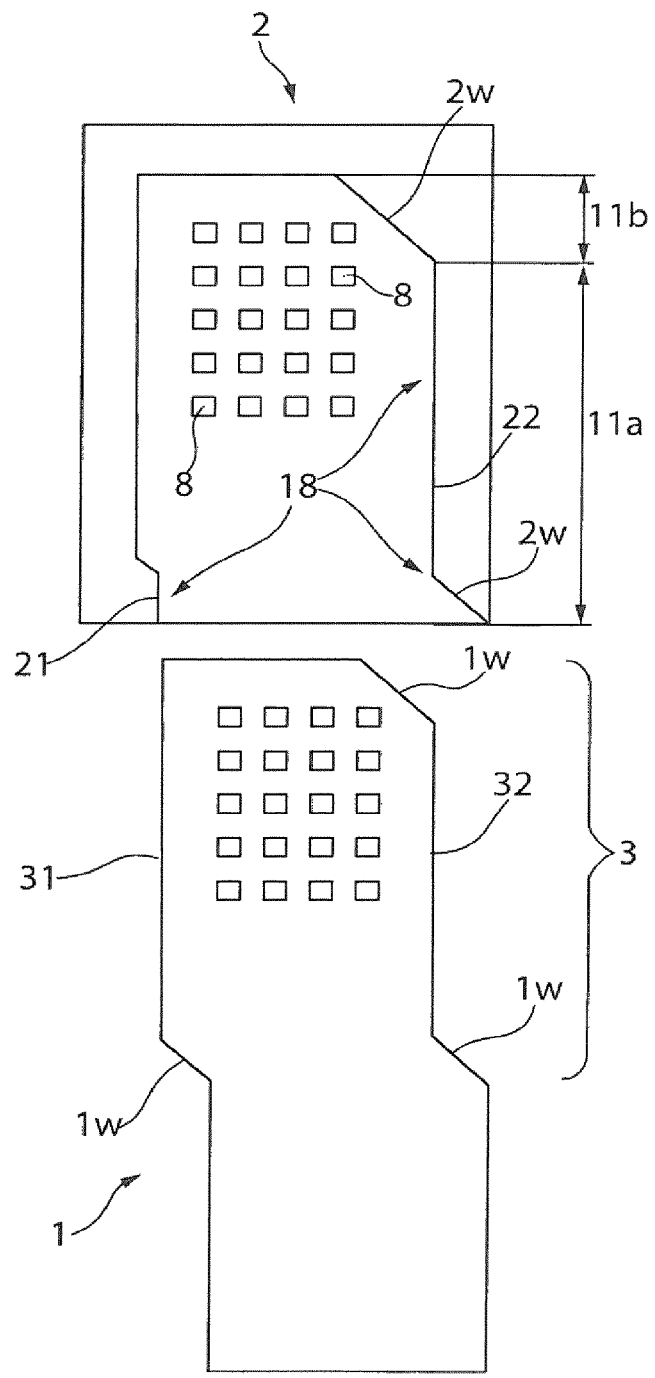
FIGS. 5a-d show views from above of a plug and socket part to illustrate the insertion procedure.

In FIG. 5a, a view from above of the plug part 1 and the socket part 2 is shown, wherein in the depiction of the socket part 2 the counterelectrode bodies 8 are also illustrated. In the shown embodiment, in the joining portion 3 the plug part 1 has twenty separately applied electrode bodies 6 on the surface 5 in the form of a chessboard pattern. The socket part 3 has just as many identical counterelectrode bodies 8 arranged in the same shape. The plug part 1 is inserted into the insertion opening 4 of the socket part 2 along an insertion guide 18, which in the direction of insertion has a first section 11 as well as a subsequent second section 12.

Figure 5D:
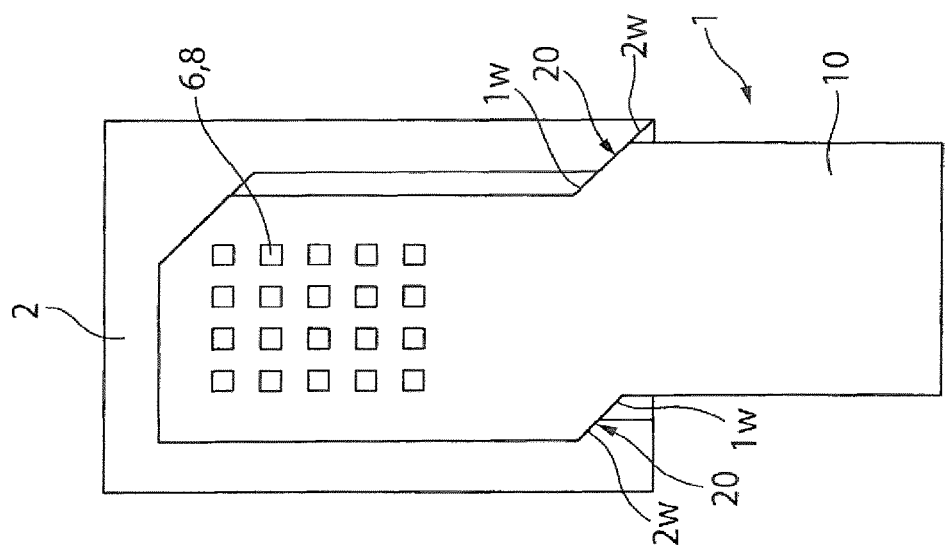
Figure 5C:
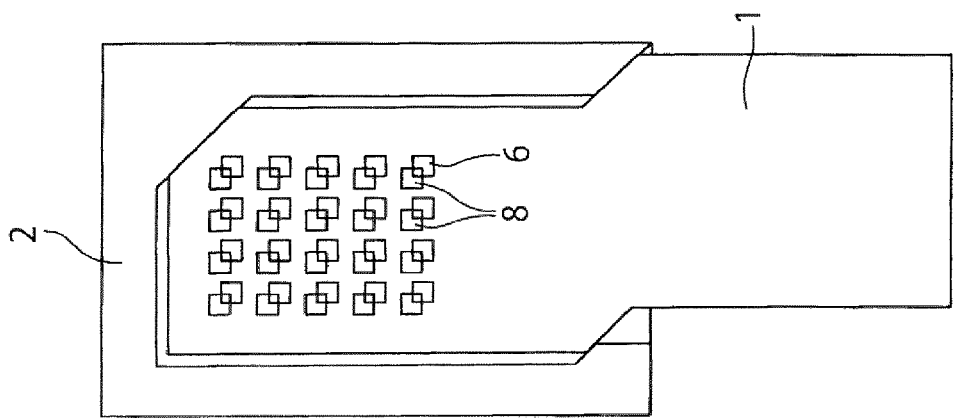
Figure 5B:
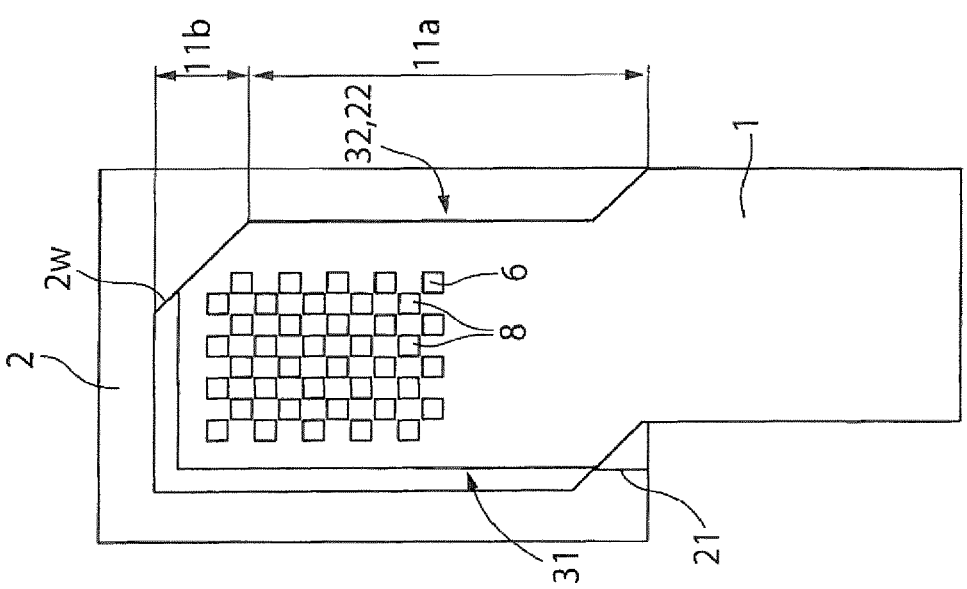

FIG. 5b shows a joining state between the plug part 1 and the socket part 2, in which the plug part 1 is inserted along the first section 11 into the socket part 2. The side walls 31, 32 of the joining portion 3 slide in a forcibly guided manner along the side delimiting walls 21, 22 within the insertion opening 4 of the socket part 2. During the insertion process the position of the plug part 1 relative to the socket part 2 is thus precisely defined. In this insertion configuration the electrode bodies 6 of the plug part 1 arranged like a chessboard are laterally offset with regard to the counterelectrode bodies 8 of the socket part 2 which are also arranged like a chessboard. This avoids mutual touching of the electrode and counterelectrode bodies 6, 8 during the insertion procedure up to the constellation shown in FIG. 5b.

As the diagonally orientated plug part-side side walls areas 1w shown in FIG. 1 touch the side wall areas 2w of the socket part 2 which also run diagonally relative to the insertion direction, the electrode and counterelectrode surfaces 6', 8' increasingly overlap each other in pairs, see FIG. 5c.

After the end position of the plug part 1 within the socket part 2 is reached, as shown in FIG. 5d, the electrode and counterelectrode surfaces 6', 8' overlap completely.

For the purpose of securing or protecting against uncontrolled sliding out of the plug part from the socket part, a web-like, structured projection can be applied to the end of the plug part which engages with a corresponding recess on the socket part and ensures that releasing the plug part from the socket part is only possible after a specific forwards or lateral pushing of the plug part relative to the insertion direction and/or through a defined force acting perpendicularly on the structured projection.

Through the lateral offset 12 between the joining portion 3 and plug portion 10, the side wall portions 1w closest to the plug portion 10 adjoin the corresponding side wall portions 2w on the socket part side, each forming fluid-tight sealing surfaces 20. With these design measures, additional polymer layers to be applied to the side walls of the socket part and/or the plug part, as shown as an example in connection with the example of embodiment illustrated in FIG. 2b, can be eliminated.

The shape of the plug part and socket part 1, 2 is not necessarily restricted to the three-dimensional shapes shown in the examples of embodiment.

In this way all-round fluid-tight sealing of the plug part 1 within the socket 2 is ensured.

LIST OF REFERENCES

1 Plug part
1w Diagonally extending side wall flanks
2 Socket part
21 Socket part lateral inner wall
22 Socket part lateral inner wall
2w Socket part diagonal wall section
3 Joining portion 31, 32 Side wall of the joining portion
3L Longitudinal direction of the plug part
3l Longitudinal direction of the joining portion
3Q Lateral direction of the joining portion
4 Insertion opening
4I Longitudinal direction of the insertion opening
5, 5' Electrically insulating surface of the plug part
6 Electrode body
6' Electrode surface
7 Electrically insulating wall portion
8 Counterelectrode body
8' Counterelectrode surface
8" Electrical connection structure
8''' Electric supply/outlet lead
9 Polymer layer
9' Recess
9" Polymer layer
9* Polymer layer on side wall
10 Plug portion
11a First section
11b Second section
12 Lateral offset
13 Stack layer composite
14 Electrical layer areas
15 Electrically insulating layer areas
16 Electrical contacts
16' Plug contact socket
17 Electrical supply/outlet leads
18 Insertion guide
19 Hygroscopic material
20 Fluid-tight sealing surface
h Thickness of the plug part
h' Opening width
2G Housing
2S Electrical interface

The invention claimed is:

1. An implantable electromechanical plug connector including a plug part and a socket part, comprising:
the plug part has a joining portion which is insertable completely into an unilaterally open insertion opening within the socket part and the plug part has an electrically insulating surface having an electrode body with a freely accessible electrode surface;
the socket part inside the unilaterally open insertion opening including an electrically insulating wall portion which laterally limits in at least parts the insertion opening and has a surface providing a counterelectrode body including a freely accessible counterelectrode surface;
the at least electrically insulating wall portion being oriented towards the electrically insulating surface of the joining portion of the plug part when the joining portion of the plug part is completely inserted into the insertion opening of the socket part so that the counterelectrode surface contacts the electrode surface;
the electrode body being raised in relation to the electrically isolating surface of the joining portion and/or the counterelectrode body is raised in relation to the surface of the electrically isolating wall portion;
an electrically insulating polymer layer configured at least in part between the electrically insulating surface of the joining portion and the surface of the electrically insulating wall portion and completely surrounding the counterelectrode surface and electrode surface which are in contact; and
the plug part includes electrically conducting layers which are each electrically insulated from each other and are configured into a stacked layer composite, with each electrically conducting layer leading to the electrically insulating surface providing a contact area and with each contact area being raised above the electrically insulating surface and contacting an electrode body.

2. The plug connector according to claim 1, wherein:
the electrically insulating polymer layer is joined to the electrically insulating wall portion within the insertion opening of the socket part and is joined to the electrically insulating surface of the joining portion of the plug part.

3. The plug connector according to claim 1, wherein:
the insulating polymer layer has a thickness corresponding to an orthogonal elevation of the counterelectrode body in relation to a surface of the electrically insulating wall portion or an orthogonal elevation of the electrode body in relation to the electrically insulating surface of the joining portion.

4. The plug connector according to claim 1, wherein:
a size and shape of the joining portion, the insertion opening and the electrically insulating polymer layer are matched to each other so that upon complete insertion of the joining portion into the insertion opening, the electrically insulating polymer layer is subjected to a compression force acting between the surface of the electrically insulating wall portion and the electrically insulating surface of the joining portion.

5. The plug connector according to claim 1, wherein:
a size and shape of the joining portion, the insertion opening and the electrically insulating polymer layer are matched to each other so that upon complete insertion of the joining portion into the insertion opening, a freely accessible electrode surface of the electrode body contacts a surface of the counterelectrode body caused by a compression force.

6. The plug connector according to claim 1, wherein:
the joining portion of the plug part has a longitudinal direction and a transverse direction, the longitudinal direction of the joining portion at least corresponding to an insertion depth of the insertion opening and on a wall side the insertion opening has an insertion guide along which the joining portion slides when forcibly guided during insertion into the insertion opening, and the insertion guide has a first section along which the joining portion is only insertable in a longitudinal direction and has an adjoining second section along which the joining portion is insertable in the longitudinal direction and in the transverse direction into the insertion opening.

7. The plug connector according to claim 1, wherein:
the electrode body on the plug part and the counterelectrode body on the socket part are configured so that electrode body and counterelectrode body surfaces are spaced apart in a transverse direction of the joining portion when the joining portion slides along the first section.

8. The plug connector according to claim 7, wherein:
a distance in a transverse direction of the joining portion between an electrode surface and a counterelectrode surface corresponds to a distance that the joining portion can be deflected after sliding in a transverse direction within the insertion opening.

9. The plug connector according to claim 1, wherein:
the plug part comprises electrically insulated electrode bodies which each have a freely accessible electrode surface, corresponding to counterelectrode bodies on the socket part.

10. The plug connector according to claim 1, wherein:
the multiple layers comprise low temperature co-fired ceramics or high temperature co-fired multilayer ceramics, and the electrode bodies raised above the electrically insulating surface comprise thick films.

11. The plug connector according to claim 1, wherein:
the socket part comprises a dimensionally stable housing in which the insertion opening is incorporated.

12. The plug connector according to claim 1, wherein:
the electrode body and counterelectrode body comprise a biocompatible conductive material selected from gold, platinum, iridium, metal alloys or conductive polymers.

13. The plug connector according to claim 1, wherein:
a normal surface of the electrically insulating surface and the electrically insulating wall portion are orthogonally or obliquely oriented, along which the joining portion of the plug part is moveable during insertion into the insertion opening of the socket part.

14. The plug connector according to claim 1, wherein:
the freely accessible counterelectrode surface of the electrode body is oriented in parallel or obliquely to the electrically insulating surface of the joining portion; and
the freely accessible counterelectrode surface of the counterelectrode body is oriented relative to the electrically insulating wall portion.

15. An implantable electromechanical plug connector including a plug part and a socket part, comprising:
the plug part has a joining portion which is insertable completely into an unilaterally open insertion opening within the socket part and the plug part has an electrically insulating surface having an electrode body with a freely accessible electrode surface;
the socket part inside the unilaterally open insertion opening including an electrically insulating wall portion which laterally limits in at least parts the insertion opening and has a surface providing a counterelectrode body including a freely accessible counterelectrode surface;
the at least electrically insulating wall portion being oriented towards the electrically insulating surface of the joining portion of the plug part when the joining portion of the plug part is completely inserted into the insertion opening of the socket part so that the counterelectrode surface contacts the electrode surface;
the electrode body being raised in relation to the electrically isolating surface of the joining portion and/or the counterelectrode body is raised in relation to the surface of the electrically isolating wall portion;
an electrically insulating polymer layer configured at least in part between the electrically insulating surface of the joining portion and the surface of the electrically insulating wall portion and completely surrounding the counterelectrode surface and electrode surface which are in contact; and
the plug part includes a plug portion which adjoins the joining portion on which an electrical contact is provided which is electrically connected to an electrode surface provided in the joining portion.

16. The plug connector according to claim 15, wherein:
the electrically insulating polymer layer is joined to the electrically insulating wall portion within the insertion opening of the socket part and is joined to the electrically insulating surface of the joining portion of the plug part.

17. The plug connector according to claim 15, wherein:
the insulating polymer layer has a thickness corresponding to an orthogonal elevation of the counterelectrode body in relation to a surface of the electrically insulating wall portion or an orthogonal elevation of the electrode body in relation to the electrically insulating surface of the joining portion.

18. The plug connector according to claim 15, wherein:
a size and shape of the joining portion, the insertion opening and the electrically insulating polymer layer are matched to each other so that upon complete insertion of the joining portion into the insertion opening, the electrically insulating polymer layer is subjected to a compression force acting between the surface of the electrically insulating wall portion and the electrically insulating surface of the joining portion.

19. The plug connector according to claim 15, wherein:
a size and shape of the joining portion, the insertion opening and the electrically insulating polymer layer are matched to each other so that upon complete insertion of the joining portion into the insertion opening, a freely accessible electrode surface of the electrode body contacts a surface of the counterelectrode body caused by a compression force.

20. The plug connector according to claim 15, wherein:
the joining portion of the plug part has a longitudinal direction and a transverse direction, the longitudinal direction of the joining portion at least corresponding to an insertion depth of the insertion opening and on a wall side the insertion opening has an insertion guide along which the joining portion slides when forcibly guided during insertion into the insertion opening, and the insertion guide has a first section along which the joining portion is only insertable in a longitudinal direction and has an adjoining second section along which the joining portion is insertable in the longitudinal direction and in the transverse direction into the insertion opening.

21. The plug connector according to claim 15, wherein:
the electrode body on the plug part and the counterelectrode body on the socket part are configured so that electrode body and counterelectrode body surfaces are spaced apart in a transverse direction of the joining portion when the joining portion slides along the first section.

22. The plug connector according to claim 21, wherein:
a distance in a transverse direction of the joining portion between an electrode surface and a counterelectrode surface corresponds to a distance that the joining portion can be deflected after sliding in a transverse direction within the insertion opening.

23. The plug connector according to claim 15, wherein:
the plug part comprises electrically insulated electrode bodies which each have a freely accessible electrode surface, corresponding to counterelectrode bodies on the socket part.

24. The plug connector according to claim 15, wherein:
the socket part comprises a dimensionally stable housing in which the insertion opening is incorporated.

25. The plug connector according to claim 15, wherein:
the electrode body and counterelectrode body comprise a biocompatible conductive material selected from gold, platinum, iridium, metal alloys or conductive polymers.

26. The plug connector according to claim 15, wherein:
a normal surface of the electrically insulating surface and the electrically insulating wall portion are orthogonally or obliquely oriented, along which the joining portion of the plug part is moveable during insertion into the insertion opening of the socket part.

27. The plug connector according to claim 15, wherein:
the freely accessible counterelectrode surface of the electrode body is oriented in parallel or obliquely to the electrically insulating surface of the joining portion; and
the freely accessible counterelectrode surface of the counterelectrode body is oriented relative to the electrically insulating wall portion.

28. An implantable electromechanical plug connector including a plug part and a socket part, comprising:
the plug part has a joining portion which is insertable completely into an unilaterally open insertion opening within the socket part and the plug part has an electrically insulating surface having an electrode body with a freely accessible electrode surface;
the socket part inside the unilaterally open insertion opening including an electrically insulating wall portion which laterally limits in at least parts the insertion opening and has a surface providing a counterelectrode body including a freely accessible counterelectrode surface;
the at least electrically insulating wall portion being oriented towards the electrically insulating surface of the joining portion of the plug part when the joining portion of the plug part is completely inserted into the insertion opening of the socket part so that the counterelectrode surface contacts the electrode surface;
the electrode body being raised in relation to the electrically isolating surface of the joining portion and/or the counterelectrode body is raised in relation to the surface of the electrically isolating wall portion;
an electrically insulating polymer layer configured at least in part between the electrically insulating surface of the joining portion and the surface of the electrically insulating wall portion and completely surrounding the counterelectrode surface and electrode surface which are in contact; and
the electrically insulating polymer layer comprises layer areas with hygroscopic properties.

29. The plug connector according to claim 28, wherein:
the electrically insulating polymer layer is joined to the electrically insulating wall portion within the insertion opening of the socket part and is joined to the electrically insulating surface of the joining portion of the plug part.

30. The plug connector according to claim 28, wherein:
the insulating polymer layer has a thickness corresponding to an orthogonal elevation of the counterelectrode body in relation to a surface of the electrically insulating wall portion or an orthogonal elevation of the electrode body in relation to the electrically insulating surface of the joining portion.

31. The plug connector according to claim 28, wherein:
a size and shape of the joining portion, the insertion opening and the electrically insulating polymer layer are matched to each other so that upon complete insertion of the joining portion into the insertion opening, the electrically insulating polymer layer is subjected to a compression force acting between the surface of the electrically insulating wall portion and the electrically insulating surface of the joining portion.

32. The plug connector according to claim 28, wherein:
a size and shape of the joining portion, the insertion opening and the electrically insulating polymer layer are matched to each other so that upon complete insertion of the joining portion into the insertion opening, a freely accessible electrode surface of the electrode body contacts a surface of the counterelectrode body caused by a compression force.

33. The plug connector according to claim 28, wherein:
the joining portion of the plug part has a longitudinal direction and a transverse direction, the longitudinal direction of the joining portion at least corresponding to an insertion depth of the insertion opening and on a wall side the insertion opening has an insertion guide along which the joining portion slides when forcibly guided during insertion into the insertion opening, and the insertion guide has a first section along which the joining portion is only insertable in a longitudinal direction and has an adjoining second section along which the joining portion is insertable in the longitudinal direction and in the transverse direction into the insertion opening.

34. The plug connector according to claim 28, wherein:
the electrode body on the plug part and the counterelectrode body on the socket part are configured so that electrode body and counterelectrode body surfaces are spaced apart in a transverse direction of the joining portion when the joining portion slides along the first section.

35. The plug connector according to claim 34, wherein:
a distance in a transverse direction of the joining portion between an electrode surface and a counterelectrode surface corresponds to a distance that the joining portion can be deflected after sliding in a transverse direction within the insertion opening.

36. The plug connector according to claim 28, wherein:
the plug part comprises electrically insulated electrode bodies which each have a freely accessible electrode surface, corresponding to counterelectrode bodies on the socket part.

37. The plug connector according to claim 28, wherein:
the layer areas with hygroscopic properties are arranged relative to of the electrical surface and counterelectrode surface so that upon complete insertion of joining portion on a plug part side into the insertion opening, moisture-induced swelling of the hygroscopic layer areas results in an increase in the compression force acting between the surface of the electrically insulating wall portion and the electrically insulating surface of the joining portion.

38. The plug connector according to claim 28, wherein:
the socket part comprises a dimensionally stable housing in which the insertion opening is incorporated.

39. The plug connector according to claim 28, wherein:
the electrode body and counterelectrode body comprise a biocompatible conductive material selected from gold, platinum, iridium, metal alloys or conductive polymers.

40. The plug connector according to claim 28, wherein:
a normal surface of the electrically insulating surface and the electrically insulating wall portion are orthogonally or obliquely oriented, along which the joining portion of the plug part is moveable during insertion into the insertion opening of the socket part.

41. The plug connector according to claim 28, wherein:
the freely accessible counterelectrode surface of the electrode body is oriented in parallel or obliquely to the electrically insulating surface of the joining portion; and
the freely accessible counterelectrode surface of the counterelectrode body is oriented relative to the electrically insulating wall portion.

42. An implantable electromechanical plug connector including a plug part and a socket part, comprising:
- the plug part has a joining portion which is insertable completely into an unilaterally open insertion opening within the socket part and the plug part has an electrically insulating surface having an electrode body with a freely accessible electrode surface;
- the socket part inside the unilaterally open insertion opening including an electrically insulating wall portion which laterally limits in at least parts the insertion opening and has a surface providing a counterelectrode body including a freely accessible counterelectrode surface;
- the at least electrically insulating wall portion being oriented towards the electrically insulating surface of the joining portion of the plug part when the joining portion of the plug part is completely inserted into the insertion opening of the socket part so that the counterelectrode surface contacts the electrode surface;
- the electrode body being raised in relation to the electrically isolating surface of the joining portion and/or the counterelectrode body is raised in relation to the surface of the electrically isolating wall portion;
- an electrically insulating polymer layer configured at least in part between the electrically insulating surface of the joining portion and the surface of the electrically insulating wall portion and completely surrounding the counterelectrode surface and electrode surface which are in contact;
- the plug part has two opposite electrically insulating surfaces oriented away from each other which each comprise an electrode body and a freely accessible electrode surface; and
- the socket part inside the unilaterally open insertion opening includes two electrically insulating wall portions which are laterally opposite each and oriented towards each other, surfaces of the wall portion providing a counterelectrode body with an accessible counterelectrode surface, and the electrically insulating wall portions are each oriented towards one of the electrically insulating surfaces of the joining portion of the plug part which, upon complete insertion of the joining portion of the plug part into the insertion opening of the socket part, the counterelectrode surfaces contact the electrode surfaces.

43. The plug connector according to claim 42, wherein: the electrically insulating polymer layer is joined to the electrically insulating wall portion within the insertion opening of the socket part and is joined to the electrically insulating surface of the joining portion of the plug part.

44. The plug connector according to claim 42, wherein: the insulating polymer layer has a thickness corresponding to an orthogonal elevation of the counterelectrode body in relation to a surface of the electrically insulating wall portion or an orthogonal elevation of the electrode body in relation to the electrically insulating surface of the joining portion.

45. The plug connector according to claim 42, wherein: a size and shape of the joining portion, the insertion opening and the electrically insulating polymer layer are matched to each other so that upon complete insertion of the joining portion into the insertion opening, the electrically insulating polymer layer is subjected to a compression force acting between the surface of the electrically insulating wall portion and the electrically insulating surface of the joining portion.

46. The plug connector according to claim 42, wherein: a size and shape of the joining portion, the insertion opening and the electrically insulating polymer layer are matched to each other so that upon complete insertion of the joining portion into the insertion opening, a freely accessible electrode surface of the electrode body contacts a surface of the counterelectrode body caused by a compression force.

47. The plug connector according to claim 42, wherein: the joining portion of the plug part has a longitudinal direction and a transverse direction, the longitudinal direction of the joining portion at least corresponding to an insertion depth of the insertion opening and on a wall side the insertion opening has an insertion guide along which the joining portion slides when forcibly guided during insertion into the insertion opening, and the insertion guide has a first section along which the joining portion is only insertable in a longitudinal direction and has an adjoining second section along which the joining portion is insertable in the longitudinal direction and in the transverse direction into the insertion opening.

48. The plug connector according to claim 42, wherein: the electrode body on the plug part and the counterelectrode body on the socket part are configured so that electrode body and counterelectrode body surfaces are spaced apart in a transverse direction of the joining portion when the joining portion slides along the first section.

49. The plug connector according to claim 48, wherein: a distance in a transverse direction of the joining portion between an electrode surface and a counterelectrode surface corresponds to a distance that the joining portion can be deflected after sliding in a transverse direction within the insertion opening.

50. The plug connector according to claim 42, wherein: the plug part comprises electrically insulated electrode bodies which each have a freely accessible electrode surface, corresponding to counterelectrode bodies on the socket part.

51. The plug connector according to claim 42, wherein: the socket part comprises a dimensionally stable housing in which the insertion opening is incorporated.

52. The plug connector according to claim 42, wherein: the electrode body and counterelectrode body comprise a biocompatible conductive material selected from gold, platinum, iridium, metal alloys or conductive polymers.

53. The plug connector according to claim 42, wherein: a normal surface of the electrically insulating surface and the electrically insulating wall portion are orthogonally or obliquely oriented, along which the joining portion of the plug part is moveable during insertion into the insertion opening of the socket part.

54. The plug connector according to claim 42, wherein:
- the freely accessible counterelectrode surface of the electrode body is oriented in parallel or obliquely to the electrically insulating surface of the joining portion; and
- the freely accessible counterelectrode surface of the counterelectrode body is oriented relative to the electrically insulating wall portion.

* * * * *